US009180284B2

(12) United States Patent
Lavoisier

(10) Patent No.: US 9,180,284 B2
(45) Date of Patent: Nov. 10, 2015

(54) DEVICE AND METHOD FOR MEASURING AND TREATING THE RIGIDITY AND ERECTION OF A PENIS AND ARTERIAL-VENOUS FLOWS

(71) Applicant: Pierre Lavoisier, Rasteau (FR)

(72) Inventor: Pierre Lavoisier, Rasteau (FR)

(*) Notice: Subject to any disclaimer, the term of this patent is extended or adjusted under 35 U.S.C. 154(b) by 241 days.

(21) Appl. No.: 13/728,242

(22) Filed: Dec. 27, 2012

(65) Prior Publication Data
US 2013/0116742 A1 May 9, 2013

Related U.S. Application Data

(62) Division of application No. 12/435,592, filed on May 5, 2009, now abandoned.

(60) Provisional application No. 61/050,318, filed on May 5, 2008.

(51) Int. Cl.
*A61N 1/18* (2006.01)
*A61N 1/00* (2006.01)
(Continued)

(52) U.S. Cl.
CPC ............... *A61N 1/00* (2013.01); *A61B 5/4393* (2013.01); *A61B 5/486* (2013.01); *A61H 9/0078* (2013.01); *A61H 19/32* (2013.01); *A61N 1/0452* (2013.01); *A61N 1/0472* (2013.01); *A61N 1/0521* (2013.01); *A61N 1/36007* (2013.01); *A61N 1/36107* (2013.01); *A61B 5/026* (2013.01); *A61B 5/02422* (2013.01); *A61H 2201/165* (2013.01); *A61H 2201/5071* (2013.01)

(58) Field of Classification Search
CPC ........... A61N 1/36007; A61N 1/36107; A61N 1/0521

USPC .................................................... 607/39, 143
See application file for complete search history.

(56) References Cited

U.S. PATENT DOCUMENTS 5,192,271 A 3/1993 Kalb et al.
5,692,520 A 12/1997 Lavoisier
(Continued)

FOREIGN PATENT DOCUMENTS

| DE | 102004023966 A | 12/2005 |
| EP | 1350465 A | 10/2003 |
| JP | 2006149566 A | 6/2006 |
| WO | 96/20753 A | 7/1996 |
| WO | 98/38914 A | 9/1998 |

*Primary Examiner* — Christopher D Koharski
*Assistant Examiner* — Michael Carey
(74) *Attorney, Agent, or Firm* — Young & Thompson

(57) ABSTRACT

The invention relates to a method for measuring the strength of the ischiocavernous muscles of a patient, the method being performed during an erection of the penis and providing a measuring and/or rehabilitation device configured to determine the strength of the ischiocavernous muscles and comprising at least one sensor, placing the sensor around the penis of the patient, measuring the variation of the intracavernous pressure, contracting the ischiocavernous muscles, and checking that the contraction causes elevation in intracarvernous pressure so as to ensure that the accurate muscles are contracted, where if the intracavernous pressure is elevated, ischiocavernous muscles are contracted during the contraction. The invention relates also to a method for treating and rehabilitating the ischiocavernous muscles comprising a step of implementing the method for measuring the strength of the ischiocavernous muscles and a step of voluntarily contracting the ischiocavernous muscles.

14 Claims, 4 Drawing Sheets

(51) Int. Cl.
  *A61N 1/36* (2006.01)
  *A61N 1/05* (2006.01)
  *A61B 5/00* (2006.01)
  *A61H 9/00* (2006.01)
  *A61N 1/04* (2006.01)
  *A61H 19/00* (2006.01)
  *A61B 5/024* (2006.01)
  *A61B 5/026* (2006.01)

(56) References Cited

U.S. PATENT DOCUMENTS

| | | |
|---|---|---|
| 5,899,875 A | 5/1999 | Millot et al. |
| 7,006,870 B1 * | 2/2006 | Whitehurst et al. ............ 607/39 |
| 2004/0039328 A1 | 2/2004 | Henley |
| 2007/0255333 A1 * | 11/2007 | Giftakis et al. ................. 607/39 |

* cited by examiner

DEVICE AND METHOD FOR MEASURING
AND TREATING THE RIGIDITY AND
ERECTION OF A PENIS AND
ARTERIAL-VENOUS FLOWS

The present invention relates to a method for measuring and treating the rigidity and erection of a penis and arterial-venous flows as well as a device for implementing this method.

Measurements taken by the device are performed either while the patient sleeps or during the day and allow, according to the results obtained, the cause of erectile dysfunctions to be determined and their progression to be controlled.

Also, the measuring device that is the object of the invention allows patient rehabilitation in the case of premature ejaculation and/or erectile dysfunction to be monitored and controlled.

Measuring the nocturnal erection of the penis, in order to be able to disassociate organic impotence from psychogenic impotence, is known. Patients with organic impotence do not have erections during the day or during paradoxical sleep, while psychogenic patients have erections during sleep but not during the daytime.

The method for measuring the strength of the ischiocavernosus muscles (IC) causing the rigidity of the penis (P) of a patient and for measuring the variation in arterial and venous flows ensuring the erection of the penis (P) of the patient consists of:

Placing a sensor around the penis (P) comprising means to receive the intracavernous pressure (ICP) and pressure variations of the penis (P), and at least one transducer integrated into or offset from the sensor allowing the pressure signal issued from the means for receiving the pressure to be transformed into an electrical signal, And connecting the sensor to a housing comprising means for amplifying and recording the signal from the transducer, means for analyzing the signal by a microcontroller allowing the fatigue state of the ischiocavernosus muscles (IC) to be measured and the variations in muscle strength of the ischiocavernosus muscles (IC) to be measured.

The measuring method consists of measuring the variations in intracavernous pressure (ICP) of the penis (P) in order to quantify the detumescence, tumescence and rigidity of the penis (P) during both day and night.

The measuring method consists of measuring the intracavernous pressure (ICP) that progressively reaches the mean systolic pressure of the penis (P).

The measuring method consists of measuring the increase in arterial inflow in the corpus cavernosum (CC) and the reduction in venous outflow during the vascular phase, which is the first penis (P) erection phase.

The measuring method consists of measuring the variations in the contraction and rigidity of the ischiocavernosus muscles (IC) surrounding the corpus cavernosum (CC) during the muscular phase, which is the second penis (P) erection phase.

The measuring method consists of continuously measuring, particularly when the patient is sleeping, the arterial inflow and venous outflow by measuring the pulse pressure (PP), pulse volume (PV) and intracavernous pressure (ICP).

The measuring method consists of measuring the Young's modulus of the corpus cavernosum (CC) allowing the compliance of said corpus cavernosum to be evaluated.

The measuring method consists of measuring and quantifying the cavernosal venous leak from the intracavernous pressure (ICP) curve.

The measuring method consists of measuring the maximum contraction (Pmax), the pressure gradient (delta P and mean delta), the surface under the curve objectifying the muscular work of each contraction, the number of peaks and the width of each peak.

The measuring method consists of measuring the ischiocavernosus muscle (IC) fatigue by measuring the angle ($\alpha$).

The measuring method consists of measuring the peaks of the ischiocavernosus muscles (IC) contractions and the variations in pulse pressure (PP) while maintaining stable pressure inside the sensor whatever the variation in the volume of the penis.

The method for treating the ischiocavernosus muscles (IC) of a patient with either erectile dysfunction or premature ejaculation or both, said patient having been diagnosed thanks to the measurement of erections taken both day and night, said measurements consisting of measurements of the strength of the ischiocavernosus muscles (IC) causing the rigidity of the penis (P) of the patient and of the arterial and venous variation in the corpus cavernosum ensuring the erection of the penis (P), said method consists of:

Placing a sensor comprising means for receiving the intracavernous pressure (ICP) and pressure variations of a penis (P), means for electro stimulating the ischiocavernosus muscles (IC), and at least one transducer integrated into or offset from the sensor allowing the pressure signal issued from the means for receiving the pressure to be transformed into an electrical signal, And connecting the sensor to a housing comprising means for amplifying and recording the signal from the transducer, means for analyzing the signal by a microcontroller allowing the electro stimulation to be controlled as a function of the fatigue state of the ischiocavernosus muscles (IC) and for controlling the muscular rehabilitation through sound, visual or tactile patterns indicating to the patient the intensity, duration and muscle contraction to be produced and the duration of the rest period between two contractions.

The method for treating a patient with erectile dysfunction or premature ejaculation comprises electro stimulation means that are constituted of electrodes controlled by a microcontroller and by the patient in order to vary the intensity.

The method for treating a patient with erectile dysfunction comprises a measuring device that establishes the diagnosis of organic impotence during the night.

The method for treating a patient with erectile dysfunction is specially indicated for patients presenting a muscular pathology with a normal vascular phase, but also for those with a mixed vascular pathology of arterial or venous and muscular origin.

The method for treating a patient with erectile dysfunction consists of placing the patient on an examination bed or on his bed, the electrodes are connected to a housing and are placed on the middle part of the penis (P), one to the right and one to the left, the electrode may also be placed on various regions of the penis, particularly along the dorsal nerve apart from the sensor.

The method for treating a patient with erectile dysfunction consists in that the patient starts the electro stimulation system of the housing and adjusts the intensity of the stimulation by using either a potentiometer placed on the housing or a virtual button placed on the screen of either the computer, a PDA or a portable telephone.

The method for treating a patient with erectile dysfunction consists in that the electro stimulation is continued until the end of the session, as with all muscle rehabilitation, since it improves the performance of the ischiocavernosus muscle (IC) rehabilitation, as well as the vasodilation of the cavernosal arteries.

The method for treating a patient with erectile dysfunction consists in that the patient verifies that his voluntary contractions cause an elevation in intracavernous pressure (ICP), which proves that the right muscles are contracted, since only the ischiocavernosus muscles (IC) raise the intracavernous pressure (ICP).

The method for treating a patient with erectile dysfunction consists in that the patient then sees a mask of muscle contractions appear on the screen that he is invited to follow, indicating the optimum duration and height of the contraction that must be made as well as the duration of the rest phase.

The method for treating a patient with erectile dysfunction consists in that the mask of muscle contractions is adjustable and established from the fatigue curve of the ischiocavernosus muscle (IC).

The method for treating a patient with erectile dysfunction consists in that modifications in the pattern indicating the modalities of the contraction to be performed will be calculated either in real time by the microcontroller during the session or between two sessions when this analysis will be done by the analysis and telecontrol center (ATC).

The method for treating a patient with premature ejaculation consists of the perineal rehabilitation that is obtained by means of the measuring device with electro stimulation of the penis (P) through electrodes positioned under the sensor, electro stimulation of the penis P allowing the ischiocavernosus muscles (IC) surrounding the corpus cavernosum (CC) to be strengthened and promoting the increase in arterial circulation and thus the erection necessary for rehabilitation.

The method for treating a patient with premature ejaculation consists in that the patient may do this rehabilitation at home according to the same method as that described for erectile dysfunction rehabilitation.

The method for rehabilitating a patient with premature ejaculation consists in that the stimulation of the vascular reflex is obtained when the patient acts by a pressure variation on the gland by small compressions between the thumb and index finger to produce an increase in the arterial flow of the cavernosal arteries such that this stimulation of the vascular reflex combined with electro stimulation of the ischiocavernosus muscles (IC) most often produces a rigid erection of the penis (P) necessary for rehabilitation.

The measuring and/or rehabilitation device comprises a sensor that is constituted of:
  A cuff integral on its inner face with a reservoir filled with a liquid allowing the intracavernous pressure (ICP) and pressure variations to be received,
  Stimulation electrodes positioned between the reservoir and the outer wall of the penis of the patient,
  And connection tubing connecting the reservoir to a photoplethysmograph and to a pressure transducer that are connected to the housing.

The measuring and/or rehabilitation device comprises a cuff connected through a first three-way valve to the photoplethysmograph measuring the displacements of a flexible membrane integral with the connection tubing in order to measure the volume of the penile pulse coming from the cavernosal arteries.

The measuring and/or rehabilitation device comprises a cuff connected through the second connection tubing and a second three-way valve to a pressure regulator to ensure stable pressure inside the reservoir of the cuff.

The measuring and/or rehabilitation device comprises a pressure regulator constituted of a cylinder comprising two chambers filled with a fluid, separated by a wall pierced with a calibrated orifice connecting said chambers between each other, said first chamber being connected to the three-way valve while said second chamber comprises a piston allowing the pressure of the fluid to be varied by means of a micrometer setting device.

The measuring and/or rehabilitation device comprises a micrometer setting device comprising a spring disposed around the operating rod of the piston in order to adjust the tension of said spring and to maintain stable pressure in the cuff while allowing high, short-duration pressure variations.

The measuring and/or rehabilitation device consists in that the cuff is held and closed around the penis of the patient by a non-elastic tie.

The measuring and/or rehabilitation device comprises a housing containing an amplifier, an analog to digital converter, a microprocessor and a removable memory card.

The measuring and/or rehabilitation device comprises a housing comprising an electro stimulation system.

The measuring and/or rehabilitation device consists in that, as the photoplethysmograph is sensitive to pressure, the latter is positioned at a certain distance from the reservoir to prevent the pressure variations from said reservoir from disturbing said photoplethysmograph.

The measuring and/or rehabilitation device consists in that the photoplethysmograph comprises a light-emitting diode and a photoelectric cell allowing a light ray to be sent in the direction of the flexible membrane and to receive the reflected ray captured by the cell, while said signal emitted by the photoplethysmograph is transmitted to the housing that allows said signal to be amplified and recorded.

The measuring and/or rehabilitation device comprises a sensor constituted of:
  An open or half-open ring comprising two branches in an arc of circumference interconnected by a flexible element,
  A strain gauge integral with the flexible element and connected to the housing.

The measuring and/or rehabilitation device consists in that the branches are flat, plate-shaped branches made in a material with high elastic deformation strength, or a material that is said to be not very deformable.

The measuring and/or rehabilitation device consists in that the flexible element connecting the branches is constituted of a thin plate of metal presenting significant elastic deformation characteristics.

The measuring and/or rehabilitation device comprises a ring comprising, on the inner face of the branches, contact areas constituted of rubber dots presenting low elastic deformation and pressing against the penis (P) of the patient so as to slightly offset the inner face of said branches of the ring.

The measuring and/or rehabilitation device comprises a ring comprising electro stimulation means that are constituted of electrodes disposed on the rubber dots.

The attached drawings, given by way of example, allow the invention, the characteristics that the invention presents and the advantages that the invention is likely to bring to be better understood:

FIG. 1 shows a measuring device 1 allowing the intracavernous pressure and blood flow at the level of the penis P of a patient to be measured.

Figure 1:
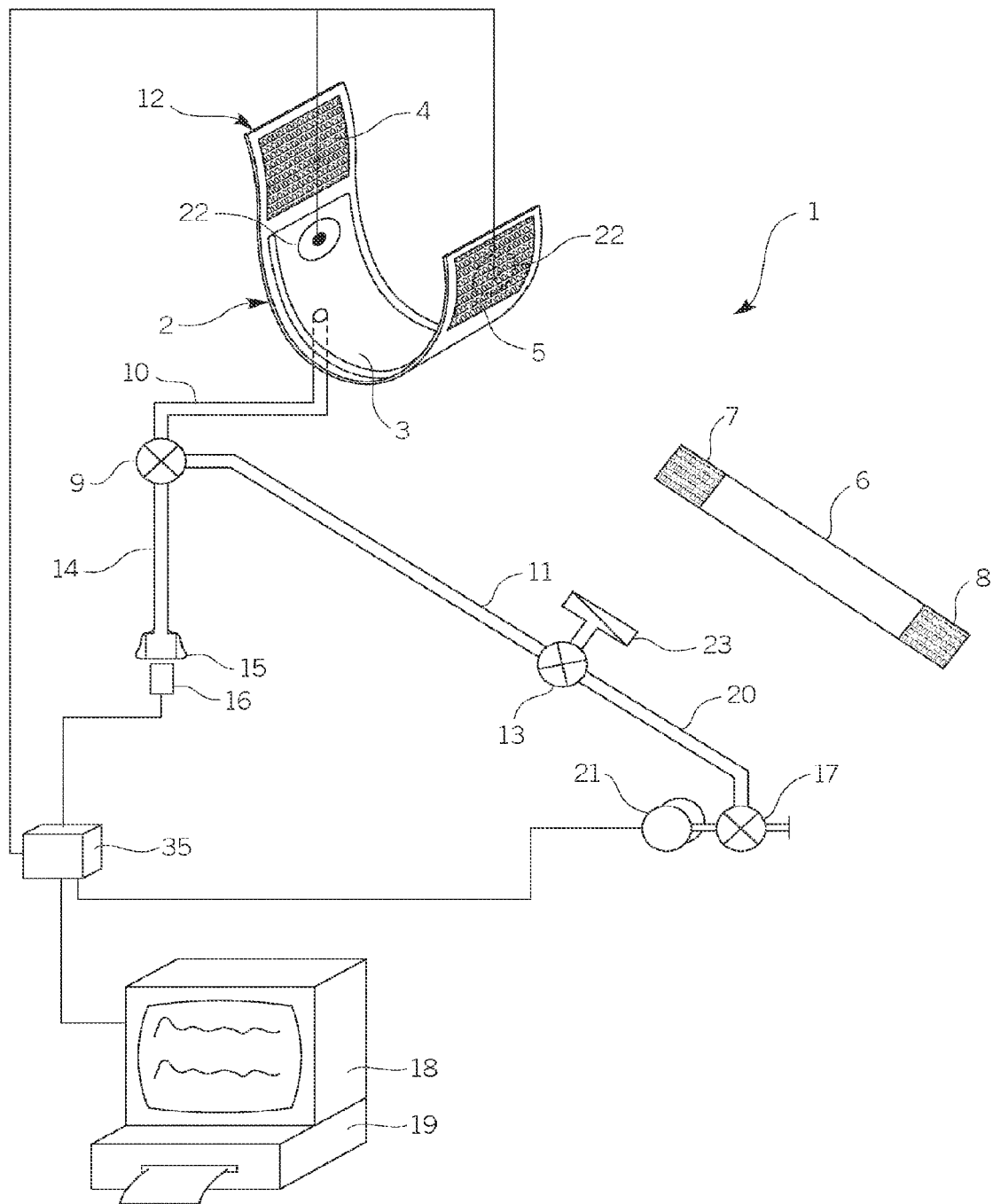
FIG. 1 is a perspective view illustrating a measuring and treating device comprising a sensor made from a non-elastic cuff according to the present invention.

Measuring device 1 is constituted of a sensor 2 formed from a cuff 12 made of a non-elastic synthetic material integral on its inner face with a reservoir 3 in plastic filled with a fluid such as water.

Cuff 12 comprises, at one of the ends of its inner face and in the extension of reservoir 3, a first self-gripping strip 4 cooperating with a second self-gripping strip 5 provided at the other end and on the outer face of said cuff 12.

The first and second self-gripping strips 4, 5 cooperate with each other to ensure closing without elastic deformation of the cuff 12 around the penis P.

Closing of the cuff 12 around the penis is completed by a non-elastic tie 6 integral on each of its opposed faces and at each end of the self-gripping strips 7, 8 allowing said tie 6 to be attached around the cuff 12.

The measuring device 1 comprises a first three-way valve 9 in which the first tubing 10 is connected in a watertight manner inside the reservoir 3 in a plastic material.

The first three-way valve 9 comprises a second tubing 11 that is connected to a second three-way valve 13 allowing the connection to a pressure regulator 23 and to a tubing 20 connected to another three-way valve 17, connected to a pressure sensor or transducer 21.

The first three-way valve 9 comprises a third tubing 14 that is sealed by a flexible membrane 15 made, for example, of latex. A photoplethysmograph 16 is placed near the flexible membrane 15 so as to be able to measure the displacements induced by the arterial pulse in the corpus cavernosum of the penis P.

The photoplethysmograph 16 comprises a light-emitting diode and a photoelectric cell allowing a light ray to be sent in the direction of the flexible membrane 15 and the reflected ray captured by the cell to be received. The signal emitted by the photoplethysmograph 16 is transmitted to a housing 35 that allows said signal to be amplified and recorded.

The housing 35 contains amplifiers, an analog to digital converter, a microprocessor, an electro stimulation system and a removable memory card. As the photoplethysmograph 16 is sensitive to pressure, the latter is positioned at a certain distance from the reservoir 3 to prevent pressure variations from said reservoir from disturbing said photoplethysmograph 16.

Also, the first three-way valve 9 allows, as a function of the measurements and controls to be performed, the photoplethysmograph 16 to be connected or disconnected, allowing it to be either used or not used.

The measuring device 1 comprises a third three-way valve 17 allowing the pressure sensor 21 to be connected to measure the pressure in reservoir 3. The signals measured by the pressure sensor 21 are transmitted to the housing 35 to be amplified and recorded.

The third three-way valve 17 allows a syringe, not illustrated, to be positioned, ensuring tubing parts 10, 11, 14 and 20 and reservoir 3 of the measuring device 1 are filled without the presence of air.

The measuring device 1 comprises electrodes 22 that are positioned under reservoir 3 so as to be in contact with the outer face of the penis P of the patient when the cuff 12 surrounds the latter. Electrodes 22 are applied to the skin of the penis P.

Electrodes 22 are connected to the housing 35 comprising an electro stimulation system allowing electrical pulses to be sent to said electrodes 22 in order to ensure controlled electro stimulation according to the measurement of IC muscle fatigue and/or the measurement of other settings, such as the measurement of the ICP of the erector muscles surrounding the corpus cavernosum of the penis P.

It is noted that the electrical stimulation of the electrodes 22 is controlled by the patient so as to be perceived without ever being painful. The patient may at any time vary the intensity that is also adjusted by the microcontroller as indicated above.

The measuring device 1 comprises at the level of the second three-way valve 13 a pressure regulator 23 that ensures stable pressure inside the reservoir 3 of cuff 12.

Figure 2:
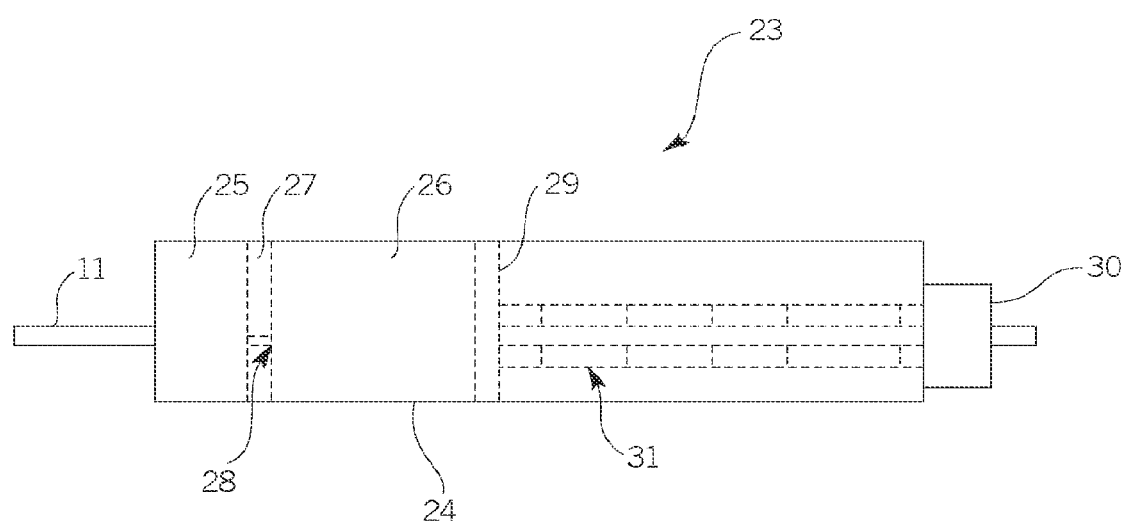
FIG. 2 is a schematic view representing a pressure regulator that may be installed on the tubing for supplying the reservoir of the measuring and treating device according to the present invention.
Figure 4:
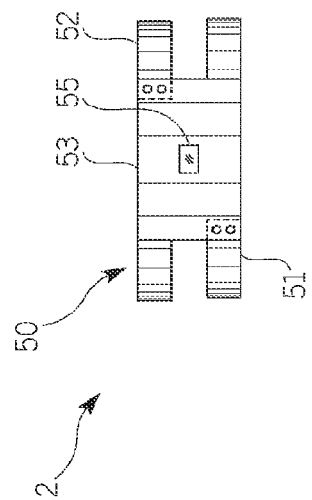
FIGS. 3 to 5 are views showing a measuring and treating device comprising a sensor made from a ring in a closed position known as "detumescence" according to the present invention.
Figure 6:
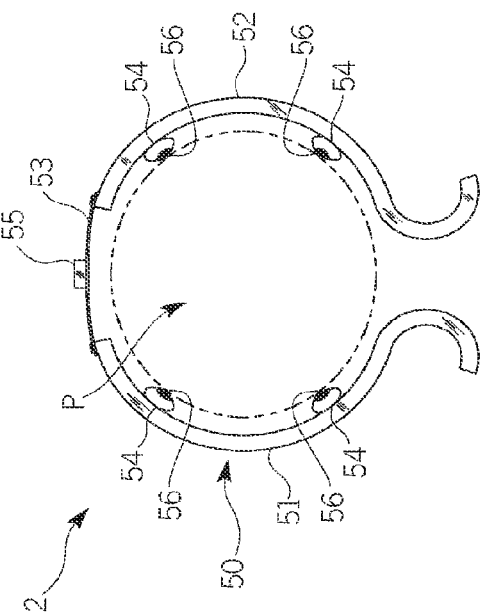
FIG. 6 is a view illustrating the ring in an open position known as "erection" according to the present invention.
Figure 3:
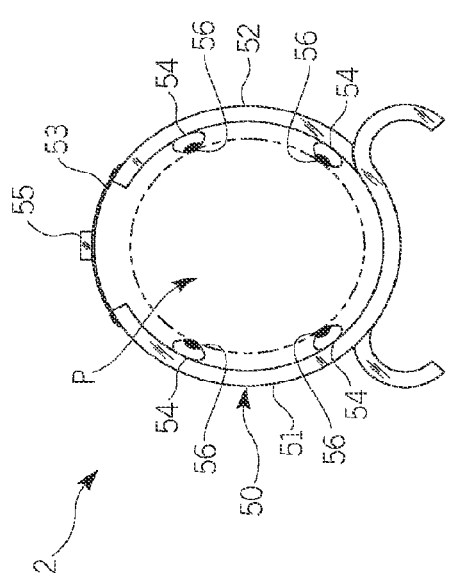
Figure 5:
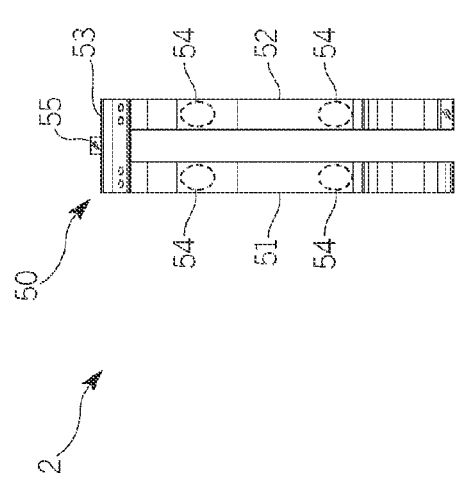

FIG. 2 shows the pressure regulator 23 that is constituted of a cylinder 24 comprising two chambers 25, 26 filled with a fluid such as water and separated by a wall 27 pierced by a calibrated orifice 28 of low diameter connecting said chambers between each other.

The first chamber 25 is connected through the second three-way valve 13 to the tubing of measuring device 1, while the second chamber 26 comprises a piston 29 allowing stable pressure to be maintained inside said chamber 26, which pressure may be adjusted by means of a micrometer setting device 30.

In fact, the micrometer setting device 30 acts on a spring 31 disposed around the operating rod of the piston 29 in order to adjust the tension of said spring and thus the pressure exerted by the piston 29 inside the second chamber 26.

Thus, the controlled displacements of the piston 29 inside the second chamber 26 allow either the fluid contained in chamber 25 to be aspirated or more fluid to be added inside the latter through the calibrated orifice 28 and thus a stable pressure to be maintained inside the single reservoir 3 whatever the variations in the volume of the penis P.

The calibrated orifice 28 allows the measuring device 1 to record short-duration pressure variations at the level of reservoir 3 and thus pressure peaks coming from ischiocavernosus muscles IC contractions of the penis P and pulse variations to be recorded while maintaining stable pressure in the cuff 12 whatever the variations in volume of the penis P, preventing painful tightening.

FIGS. 3 to 6 represent a measuring device 1 comprising a sensor that is constituted of an open ring or half ring 50 comprising two branches 51, 52 in an arc of circumference interconnected at the top of the circular profile by a flexible element 53.

Branches 51, 52 are plate-shaped flat branches made in a material with high elastic deformation strength, or a material that is said to be not very deformable.

Ring 50 comprises on the inner face of branches 51, 52 contact areas pressing against the penis so as to slightly offset the inner face of said branches from the latter.

The contact areas are made through rubber dots 54 presenting low elastic deformation in order to promote cutaneous circulation and to prevent a tourniquet from forming during the erection.

Ring 50 comprises electro stimulation means that are constituted of electrodes 56 disposed on the rubber dots 54 in order to ensure controlled electro stimulation allowing the best measurement of the ischiocavernosus muscle IC surrounding the corpus cavernosum of the penis P.

The flexible element 53 connecting the branches 51, 52 is constituted of a thin plate of metal presenting significant elastic deformation characteristics.

The flexible element 53 comprises on one of its faces a strain gauge 55 that is connected by any means to housing 35 of the measuring device 1.

Branches 51, 52 of ring 50 may cross with respect to each other to constitute a closed ring. In this case, it suffices to act on the free end of branches 51, 52 to obtain a slight deformation of the flexible element 53 in order to be able to place the ring 50 around the penis P of the patient.

The structure and composition of the ring 50 enables it to be adapted to different volumes and circumferences of the penis P without restricting the blood circulation within the latter.

Thus, variations in the volume of the penis P are obtained by the larger or smaller opening of the ring 50 that is measured by the deformation of the flexible plate or base plate 53 and recorded by the gauge 55.

Also, variations in pressure are obtained by deformation of the base plate 53 according to its elasticity and are measured and recorded by the gauge 55.

Due to its conformation, ring 50 enables passing from a closed position known as "detumescence" to an open position known as "erection." The different positions of the ring 50 allow variations in pressure and volume of the penis P to be measured; the compliance of the latter is thus delta V/delta P.

Figure 7:
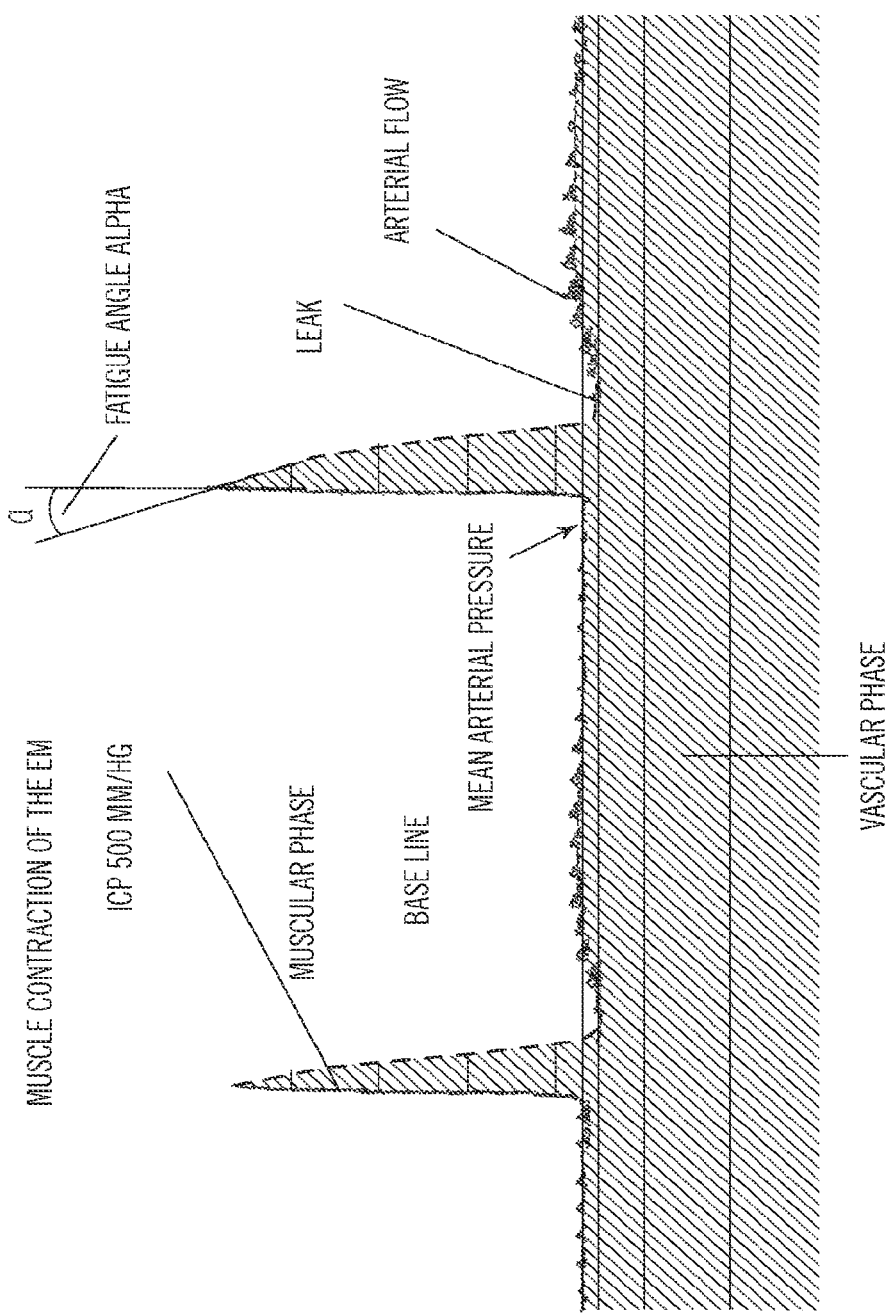
FIG. 7 is a diagram showing the variations in pressure measured by the measuring and treating device according to the present invention.

Erection and Physiological Measurements (FIG. 7)

Penile erection quality is only the reflection of the intracavernous pressure (ICP). Detumescence or the state of rest is the consequence of low intracavernous pressure (ICP) on the order of 10 to 20 mm/hg.

Increasing the intracavernous pressure (ICP) leads to an increase in the volume of the penis and in its hardness.

Tumescence is the consequence of a mean intracavernous pressure (ICP) on the order of 100 mm/hg to 120 mm/hg.

Rigidity is the consequence of high intracavernous pressure (ICP), greater than 400 mm/hg.

Increasing the volume during an elevation in intracavernous pressure (ICP) is proportional to the elasticity of the corpus cavernosum (CC) defining the delta V/delta P compliance.

During an erection, the intracavernous pressure (ICP) progressively reaches the mean systolic pressure, or 100 to 120 mm/hg. The maximum volume of the penis is reached when penile elasticity is blocked by the tunica albuginea, allowing the maximum volume of the penis P to be measured. This mean systolic pressure measurement is illustrated by the base line in FIG. 7.

The tunica albuginea is a membrane with low compliance that surrounds the corpus cavernosum (CC), preventing its dilation, which enables the pressure to be elevated.

The vascular phase is the first phase of erection, or tumescence, the consequence of the increase in the arterial-venous flows (AVF), that is the inflow (arterial) into the corpus cavernosum (CC) associated with a reduction in outflow (venous).

The second phase, known as the muscular phase, only becomes effective once the first vascular phase is obtained. Contraction of the ischiocavernosus muscles (IC) surrounding the corpus cavernosum (CC) increases the intracavernous pressure (ICP) from 100 m/hg to 400, or 600 mm/hg or more, which constitutes penile rigidity.

This significant elevation in intracavernous pressure (ICP) is only possible thanks to the tunica albuginea preventing the corpus cavernosum (CC) from dilating.

To obtain a rigid erection, thus having a high intracavernous pressure (ICP) due to contraction of the ischiocavernosus muscles (IC), the vascular phase must precede the muscular phase.

In fact, if the vascular phase is not achieved, the tension exerted on the tunica albuginea is low and consequently its elasticity is high. The muscle contraction is then weak or not effective.

This is explained and measured by the Young's modulus of the corpus cavernosum (CC) and the tunica albuginea.

Young's modulus indicates that when a low tension is exerted on the tunica albuginea, its elasticity is high, while with a high tension, its elasticity diminishes.

If the intracavernous pressure (ICP) is low, the Young's modulus of the tunica albuginea is low, leading to a slight variation in intracavernous pressure (ICP), (delta ICP), caused by the contraction of the ischiocavernosus muscles (IC), since the pressure variation (delta ICP) is absorbed by the elasticity of the tissues.

On the other hand, at the end of the vascular phase, if the tumescence is complete, the tension exerted on the tunica albuginea is high, its elasticity is low, the Young's modulus is high, causing a pressure variation (delta ICP) that is poorly absorbed by the elasticity of the tissues and thus significant variations in intracavernous pressure (ICP).

The three most frequent causes of impotence are:
Arterial causes due to reduction in inflow,
Leaks due to the absence of reduction in outflow, these two causes being disturbances in the arterial-venous flows (AVF),
Muscular causes due to a reduction in muscle strength of the ischiocavernosus muscles (IC).

The measuring device 1 comprising either a sensor 2 constituted of a cuff 12 or a sensor formed from a ring 50 allows the needs stated above to be met.

Arterial Causes or Inflow Measurement

Measuring inflow is conventionally done by the Doppler effect. The Doppler effect measures the speed of blood but does not measure the flow, unless the diameter of the vessels is known, which is possible but not very precise. Variations in flow can be measured by measuring the surface under the Doppler signal curve, but these are only variations.

In addition, Doppler effect measurements are not adapted to continuous measurements since the investigator is required to be continuously present. This is due to the fact that the position of the Doppler probe must be maintained with a precise angle with relation to the artery, the least movement "losing" the signal.

Doppler is thus poorly adapted to continuous measurements, especially during sleep.

This is the reason for which the measuring device 1 according to the present invention ensures that inflow is continuously measured, particularly during sleep, by measuring the pulse pressure (PP) and pulse volume (PV).

The measuring device 1 allows arterial-venous flows (AVF), that is, the flow of the cavernosal arteries, or inflow, to be measured. This method is based on measuring the pulse pressure (PP). In fact, during nocturnal or diurnal recordings, we observe, after injection of a vasodilator, that variations in pressure generated by the pulse are visible. These pressure variations correlate with the blood flow under certain conditions.

Measuring device 1 allows the arterial-venous flows (AVF), that is, the inflow, to be continuously measured according to two different methods:

Either by pulse volume (PV), which requires two different sensors, one pressure sensor to measure the intracavernous pressure (ICP) and the other a photoplethysmograph (PPL) to measure the flow, Or by pulse pressure (PP) with a single sensor that simultaneously measures the intracavernous pressure (ICP) and pressure variations in the pulse pressure (PP).

Leaks Due to the Absence of Reduced Outflow

Venous leaks, or cavernosal leaks, or cavernosal venous leaks are the main causes of [the absence of] reduced outflow.

This is due to a reduction in elasticity or compliance of the corpus cavernosum (CC) that restricts its dilation (and thus erection), but especially hinders the reduction in arterial-venous flows (AVF) and more particularly the outflow.

In fact, the venous network of the corpus cavernosum (CC), which enables the outflow, is at the periphery of the corpus cavernosum (CC) under the tunica albuginea, and is thus situated between the corpus cavernosum (CC) and the tunica albuginea.

During dilation of the corpus cavernosum (CC), whose compliance is high, the venous network is compressed between the corpus cavernosum (CC) and the tunica albuginea, whose compliance is low.

If, for pathological reasons, the compliance of the corpus cavernosum (CC) diminishes, venous compression cannot take place. The arterial-venous flows (AVF), and more particularly the outflow, are not reduced; we then speak of a venous leak that is in fact a cavernosal venous leak not connected to a venous pathology but rather to a cavernosal pathology.

In this case, even if the outflow is sufficient, the intracavernous pressure (ICP) cannot rise if the leak is significant. In case of a slight leak, the inflow may compensate for this loss by increasing the flow.

The measuring device 1 allows the leak from the intracavernous pressure (ICP) curve to be measured.

The curve illustrated in FIG. 7 represents the intracavernous pressure (ICP), wherein the base line indicates the level of the intracavernous pressure (ICP) outside of a contraction of the ischiocavernosus muscles (IC). As the sudden elevation in pressure corresponds to a contraction of the ischiocavernosus muscles (IC), it perfectly correlates with the electromyographic activity of the ischiocavernosus muscles (IC).

During sleep, these contractions are involuntary and during a rehabilitation session they are voluntary, but the appearance of the curve is identical.

The measuring device 1 enables a drop in intracavernous pressure (ICP) below the base line just after a voluntary contraction (muscle contraction), then an increase in several seconds to regain the level of pressure obtained just before the contraction, to be demonstrated.

In fact, when the intracavernous pressure (ICP) is stable, the value of the intracavernous pressure (ICP) is none other than the mean systolic pressure; the arterial-venous flows (AVF) and more particularly the inflow are then equal to the outflows since the intracavernous pressure (ICP) is stable, allowing the outflow to be measured.

The sudden drop in intracavernous pressure (ICP) is caused by the muscle contraction. In fact, outside of these contractions, a sudden drop in the intracavernous pressure (ICP) is never observed. This pressure drop is due to a slight reduction in the volume of blood contained in the corpus cavernosum (CC).

Thus, this is a leak caused by a muscle contraction that forces out a quantifiable volume of blood. In fact, we can count the number of heart beats necessary for its filling, and knowing the pulse volume we can deduce the leak volume during a contraction.

For a normal patient, the corpus cavernosum (CC) compliance is high and the intracavernous pressure (ICP) sufficiently compresses the venous network to allow the arterial-venous flows (AVF), and more particularly the outflows, to remain equal to the inflows, this is the physiological leak.

During a contraction of the ischiocavernosus muscles (IC), the sudden elevation in intracavernous pressure (ICP) is due to an extrinsic compression of the tunica albuginea by the ischiocavernosus muscles (IC). This pressure is transmitted to the inner face of the tunica albuginea and then to the corpus cavernosum (CC), which causes a sudden elevation in the intracavernous pressure (ICP) and a strong compression of the venous network.

On the other hand, if the compliance is low, the transmission of pressures is not sufficient to obtain a complete compression of the veins, which forces a volume of blood outside of the corpus cavernosum (CC).

The leak is measured from the surface of the triangle observed just after a voluntary muscle contraction.

For a pathological patient, especially if a leak is suspected, measuring the Young's modulus of the corpus cavernosum (CC) becomes fundamental since it enables the corpus cavernosum (CC) compliance to be evaluated, and thus the cause of the leak to be confirmed.

Several techniques exist to measure the Young's modulus of the corpus cavernosum (CC). Of course this measurement, as well as the evaluation of the corpus cavernosum (CC) compliance, may be carried out with the measuring and control device according to the present invention.

Muscular Causes Due to a Reduction in Muscle Strength of the Ischiocavernosus Muscles (IC).

Muscle contraction is visible on the curve illustrated in FIG. 7; this is a muscle contraction that perfectly correlates with the electromyographic EMG activity of the ischiocavernosus muscles (IC).

There is even a causal link between the peaks recorded and the contraction of the ischiocavernosus muscles (IC). Contraction of the ischiocavernosus muscles (IC) constitutes penile rigidity.

The measuring and control device 1 according to the present invention enables the following measurements to be taken, either at night or during an artificial erection:

Pmax: Maximum contraction, delta P: The pressure gradient recorded above the base line, The mean delta during a session or a night.

The surface under the curve of each contraction objectifying the work provided by the muscle and the average of these surfaces, The number of peaks, The width of each peak measured at its base and their average, Measurement of the leak, Inflows and outflows, Arterial-venous flows (AVF).

Nocturnal Recording Procedure

The measuring device 1 constituted of the sensor 2, 50 according to the present invention allows the rehabilitation of patients with erectile dysfunction and premature ejaculation to be monitored, these patients having been diagnosed thanks to the measurement of their nocturnal erections.

Measurement of nocturnal erections is essential for determining the type of impotence, that is, psychogenic impotence versus organic impotence.

The measuring device 1 utilized for nocturnal measurements is practically the same as that described previously, it differs in that it is not connected to a computer screen 18, data are stored in a removable memory and there is no electro stimulation system.

The analysis software is also a little different, since it particularly calculates the duration of erections and the number of erections and establishes zooms on each erection.

The recording is done at home, without sleep recording, but may also take place in a sleep laboratory.

If the recording is done at home, the housing 35 is entrusted to the patient, who comes to pick it up at the physician's office.

Prior to this, the physician will have programmed the housing 35 in order to record the characteristics of the patient (date, last name, first name, age, tobacco use, pathologies are detailed, glycemia, cholesterol, medications, and all other information likely to intervene in his erectile function).

The physician, after having recorded the data of the patient, verifies the battery charge, calibration and proper functioning of the recording. He disconnects the housing 35 from his computer and entrusts it to the patient, accompanied by a memo explaining the connection.

At bedtime, the patient places, for example, the cuff 12 of the sensor 2 integral with reservoir 3 on his penis P. Reservoir 3 is connected by tubing parts 10, 11 and 20 and three-way valves 9, 13 and 17 to the pressure sensor 21 that is connected to housing 35. Tubing parts 10, 11 and 20 are provided in a length of at least one meter allowing the patient to place the assembly nearby on his bedside table or on the floor.

Once lying down, the patient starts the measuring device 1 by using the on-off button provided on housing 35, a blinking red LED indicating that the recording has started. An automatic zero reset of the pressure sensor 21 is performed by the software after several minutes of recording.

After waking up, the patient verifies that the LED is still lit, attesting to the fact that the recording was not interrupted during the night. The patient turns the housing 35 off.

The patient starts the same operations described above over again on the following nights.

After three consecutive nights, the patient brings the measuring device 1 back to the physician, who transfers the data contained in a removable memory disposed in housing 35 to his computer.

The data are partially or completely analyzed by the software and/or then sent, via the Internet, in the database of the analysis and telecontrol center (ATC). A hard copy of the curves, zooms and calculations of each night will be printed, and the complete analysis will be possibly sent by the analysis and telecontrol center (ATC).

This nocturnal recording procedure may be carried out with the measuring device 1 constituted of the open or half open ring 50.

Erectile Dysfunction Treatment Procedure

The measuring device 1 constituted of the sensor 2. 50 according to the present invention allows patients with erectile dysfunctions to be treated. This treatment may be carried out either at the attending physician's office or at the patient's home.

When the diagnosis of organic impotence is established during the night by the measuring device 1, the latter also enables treatment thanks to several modifications in the software.

Treatment is obtained by rehabilitation that is specially indicated for patients presenting a muscular pathology having a normal vascular phase, but also for those having a mixed vascular pathology of arterial or venous and muscular origin.

This rehabilitation may be carried out either by means of the cuff 12, or by means of the open or half open ring 50 equipped with electrodes 56 described previously. By way of a non-limiting example, only rehabilitation with cuff 12 was described, knowing that the rehabilitation will be substantially identical with ring 50.

The patient is placed on an examination bed or on his bed, electrodes 22 connected to housing 35 are placed on the middle part of penis P, one at the right and the other at the left; they may also be placed on various regions of the penis, particularly along the dorsal nerve apart from the cuff 12.

Reservoir 3 of cuff 12 was filled beforehand by the physician with 2 CC of water through a syringe, while pressure sensor 21 is connected to housing 35. As the patient does not have to handle the syringe, it will remain at the office of the physician.

Housing 35 contains an amplifier, an analog to digital converter, a microprocessor and an electro stimulation system.

The housing 35 is connected by a USB cable or by a Bluetooth system or by another system to a computer 18. The device is turned on and the physician proceeds with resetting the pressure sensor 21, either automatically after one minute of operation, or by using a virtual button situated on the screen of either the computer 18, or a PDA, or a portable telephone allowing the housing 35 to be controlled (off, on, reset, electro stimulation).

The electro stimulation system of the housing 35 is started, and the patient adjusts the intensity of the stimulation either by using a potentiometer placed on the housing 35 or by using a virtual button situated on the screen of either the computer 18, or a PDA, or a portable telephone.

An intracavernous injection of a vasodilator is then carried out in all patients for whom the erection is insufficient following stimulation of the vascular reflex to cause an erection. This injection also participates in the improvement of the arterial component.

The electro stimulation is continued until the end of the session, as with all muscle rehabilitation, since it improves the rehabilitation performance of the ischiocavernosus muscles (IC) as well as the vasodilation of the cavernosal arteries.

The patient must then verify that the voluntary contractions cause an elevation in intracavernous pressure (ICP), which proves that the right muscles are contracted, since only the ischiocavernosus muscles (IC) raise the intracavernous pressure (ICP).

The patient then sees a mask of muscle contractions appear on the screen, that he is invited to follow, which indicates the optimal duration and height of the contraction that must be made as well as the duration of the rest phase.

This adjustable mask is established from the fatigue curve of the ischiocavernosus muscles (IC). It enables the rehabilitation to be optimized. In fact, insufficient work will be synonymous with the absence of improvement but, conversely, an overly intense rehabilitation will exhaust the ischiocavernosus muscles (IC). Thus, an optimal intensity exists, calculated as a function of the fatigue curve.

The fatigue of the ischiocavernosus muscle (IC) is calculated by measuring the angle $\alpha$ formed on the curve. For a given peak width, the smaller the angle $\alpha$, the greater the fatigue (FIG. 7).

Modifications in the pattern indicating the modalities of the contraction to be made will be calculated either in real time or during the session or between two sessions when this analysis will be carried out by the analysis and telecontrol center (ATC).

Procedure for Treating Premature Ejaculation

The measuring device 1 constituted of the sensor 2, 50 according to the present invention allows patients with premature ejaculation problems to be treated.

Premature ejaculation (PE) affects 30% of the male population. Currently, the most effective treatment consists of using certain antidepressant agents that have the advantage of being effective from the start of treatment but the disadvantage of not treating premature ejaculation (PE).

In fact, upon suspension of the drug treatment and in the large majority of cases, the symptom will reappear.

The second effective treatment utilizes a local anesthetic that reduces the sensitivity of the gland, its efficacy is real but it sometimes reduces the pleasure of the two partners. As with chemical treatment, the symptom will reappear upon suspension of the treatment.

The premature ejaculation treatment that is the object of the invention is obtained by perineal rehabilitation by means of the measuring device 1 with electro stimulation of the penis P through electrodes 22 positioned under reservoir 3 integral with cuff 12 or electrodes 56 positioned inside ring 50.

This electro stimulation of the penis P allows the ischiocavernosus muscles (IC) surrounding the corpus cavernosum (CC) to be strengthened and the increase in arterial circulation, and thus the erection necessary for rehabilitation, to be promoted.

Rehabilitation may, for example, be carried out at the home of the patient who has a housing 35 that may be connected via Bluetooth to his computer or to a PDA or to his portable telephone, as with the evaluation of erectile dysfunction, or through a screen integral with housing 35.

The session is designed in the same manner; the only thing that is different is the fashion in which the erection necessary for strengthening the ischiocavernosus muscles (IC) is produced.

The patient is invited to place the cuff 12 equipped with electrodes 22 on his penis P so that the reservoir 3 is in contact with the latter or the open ring 50 comprising electrodes 56. The patient turns housing 35 on and ensures that the connection operates by verifying that a pressure variation (by pressing on the cuff) results in a pressure elevation on the screen of the computer.

Stimulation of the vascular reflex is obtained by a pressure variation on the gland by small compressions between the thumb and index finger to produce an increase in the arterial flow of the cavernosal arteries. This stimulation of the vascular reflex combined with electro stimulation of the ischiocavernosus muscles (IC) most often produces a rigid erection of the penis (P).

This stimulation most often causes an erection in patients with premature ejaculation without any stimulation of the ejaculatory reflex.

When stimulation of the vascular reflex will not be sufficient for initiating the erection, the use of a vasodilator product by oral route or injection will be instituted.

In addition, it must be understood that the previous description was only given by way of example and that it in no way limits the field of the invention from which one will not depart by replacing the details of embodiment described by any other equivalents.

The invention claimed is:

1. A method for measuring the strength of the ischiocavernous muscles of a patient with either erectile dysfunction or premature ejaculation or both, the method being performed during an erection of the penis and comprising the following steps:
   (a) providing, to the patient, a measuring and/or rehabilitation device configured to determine the strength of the ischiocavernous muscles of the penis, the device comprising at least one sensor;
   (b) placing the sensor around an outer surface of the penis of the patient;
   (c) via the at least one sensor, measuring the variation of intracavernous pressure of the penis;
   (d) externally stimulating the ischiocavernous muscles of the penis using a pair of electrodes; and
   (e) determining whether the stimulating causes an elevation in intracavernous pressure,
   wherein a positive detection of said elevation in intracavernous pressure indicates that ischiocavernous muscles were contracted during the stimulation.

2. The measuring method according to claim 1, further comprising:
   measuring a Young's modulus of a corpus cavernosum of the penis to evaluate a compliance of said corpus cavernosum.

3. A method for treating and rehabilitating the ischiocavernous muscles, comprising:
   measuring a strength of the ischiocavernous muscles, said measuring comprising the sub-steps of
   (a) providing, to the patient, a measuring and/or rehabilitation device configured to determine the strength of the ischiocavernous muscles of the penis, the device comprising at least one sensor,
   (b) placing the sensor around the penis of the patient,
   (c) via the at least one sensor, measuring the variation of intracavernous pressure of the penis,
   (d) externally stimulating the ischiocavernous muscles of the penis using a pair of electrodes, and
   (e) determining whether the stimulation causes an elevation in intracavernous pressure;
   voluntarily, by the patient, contracting the ischiocavernous muscles; and
   determining whether the voluntary contraction causes an elevation in intracavernous pressure.

4. The method of treating and rehabilitating according to claim 3, further comprising:
   determining i) a fatigue of the ischiocavernous muscles of the patient in order to adjust an intensity and duration of ischiocavernous muscle contractions to be produced, and ii) the duration of a rest period between two produced contractions, as a function of the said fatigue of the ischiocavernous muscles of the patient, a state of fatigue being determined by measuring an angle $\alpha$ formed on a curve representing the intracavernous pressure during voluntary contractions of the ischiocavernous muscles.

5. The method of treating and rehabilitating according to claim 3, further comprising:
   displaying a mask of the ischiocavernous muscles contraction to the patient in order to indicate to the patient an optimum duration and height of a contraction that must be made, as well as the duration of the rest period between two contractions.

6. The method of treating and rehabilitating according to claim 5, wherein the mask of the ischiocavernous muscles contraction is adjustable and established from the fatigue state of the ischiocavernous muscles.

7. The method of treating and rehabilitating according to claim 3, further comprising:
calculating patterns for indicating to the patient the intensity, duration and ischiocavernous muscles contraction to be produced and the duration of the rest period between two contractions, said calculating step being performed in either real time during a session or between two sessions by way of an analysis and telecontrol center.

8. The method of treating and rehabilitating according to claim 3, wherein the measuring and/or rehabilitation device comprises the pair of electrodes, the electrodes configured to electro-stimulate the ischiocavernous muscles, and the electrodes configured to be placed to the skin of the penis wherein the ischiocavernous muscles are stimulated by said electrodes.

9. The method of treating and rehabilitating according to claim 8, wherein the electrodes are placed on the middle part of the penis of the patient.

10. The method of treating and rehabilitating according to claim 8, wherein the electrodes are configured to electro-stimulate indirectly the ischiocavernous muscles via the dorsal nerve.

11. The method of treating and rehabilitating according to claim 8, further comprising:
adjusting an intensity of the electro-stimulation, either by using a potentiometer placed on the housing, or by using a virtual button situated on a screen of either the computer or a PDA or a portable telephone.

12. The method of treating and rehabilitating according to claim 8, wherein the sensor of the measuring and/or rehabilitation device is constituted of a cuff, an inner face of the cuff including a reservoir filled with a liquid configured to respond to the intracavernous pressure and pressure variations.

13. The method of treating and rehabilitating according to claim 8, wherein the sensor of the measuring and/or rehabilitation device is constituted of an open or half-open ring, comprising two branches in an arc of circumference interconnected by a flexible element.

14. The method of treating and rehabilitating according to claim 3, wherein a stimulation of the vascular reflex is obtained by the pressure variation on the penis by small compressions between the thumb and index finger to produce an increase in arterial flow of cavernosal arteries of the penis, said stimulation of the vascular reflex, combined with electro-stimulation of the ischiocavernous muscles, intended to produce a rigid erection of the penis as necessary for perineal rehabilitation.

* * * * *